United States Patent [19]

Pourfarzaneh et al.

[11] Patent Number: 5,310,656
[45] Date of Patent: May 10, 1994

[54] VITAMIN B12 ASSAY

[75] Inventors: Mohammad T. Pourfarzaneh, Alameda; George W. Katsilometes, Davis, both of Calif.

[73] Assignee: Tritech Partners, Tarrytown, N.Y.

[21] Appl. No.: 898,240

[22] Filed: Jun. 12, 1992

Related U.S. Application Data

[63] Continuation of Ser. No. 371,324, Jun. 26, 1989, abandoned.

[51] Int. Cl.$^5$ ............... G01N 33/82; G01N 33/53; G01N 33/537; G01N 33/543
[52] U.S. Cl. .................. 435/7.93; 435/7.1; 435/7.9; 435/7.92; 435/975; 436/501; 436/526; 436/815; 436/822
[58] Field of Search ............ 530/388.2; 435/7.9, 435/7.93, 7.1, 7.92, 975; 436/501, 503, 526, 536, 538, 505, 815, 822; 536/25

[56] References Cited

U.S. PATENT DOCUMENTS

| | | | |
|---|---|---|---|
| 4,115,534 | 9/1978 | Ithakissios et al. | 424/1 |
| 4,188,189 | 2/1980 | Allen | 23/230.3 |
| 4,300,907 | 11/1981 | Mansbach et al. | 23/230 B |
| 4,355,018 | 10/1982 | Hansen et al. | 424/1 |
| 4,447,528 | 5/1984 | Ellis et al. | 435/7 |
| 4,451,571 | 5/1984 | Allen | 436/505 |
| 4,465,775 | 8/1984 | Houts | 436/503 |
| 4,659,678 | 4/1987 | Forrest et al. | 436/512 |
| 5,187,107 | 2/1993 | Watkins et al. | 436/505 |
| 5,227,311 | 7/1993 | Kuemmerle et al. | 436/501 |

OTHER PUBLICATIONS

R. Gullberg, "Sensitive Test for Antibody Type I to Intrinsic Factor", Clin. exp. Immunol. 9:833–838 (1971).

M. Muckerheide, J. Wolfman, D. Rohde and G. McManamy, "Studies on a Radioassay for Intrinsic Factor Antibody: Comparison of Methods and False Positive Results due to Elevated Serum B$_{12}$ Levels," Am. J. Clin Path. 82(3): 300–304 (1984).

"Vitamin B$_{12}$ Assays" in Saunders Dictionary and Encyclopedia of Laboratory Medicine and Technology, Bennington, J. L. ed, W. B. Saunders Co. p. 1594 (1984).

C. E. Hoffmann, E. L. R. Stokstad, B. L. Hutchings, A. C. Dornbush and T. H. Jukes, "The Microbiological Assay of Vitamin B$_{12}$ with Lactobacillus Leichmannii", J. Biol. Chem. 181:635–644 (1949).

H. M. Waters, J. A. Thornton, R. F. Stevens, A. H. Gowenlock, J. E. Maciver and I. W. Delamore, "Comparative studies of a new commercial kit for the estimation of vitamin B$_{12}$ in serum", J. Clin. Pathol. 34:972–978 (1981).

R. J. LeFebvre, A. S. Virji and B. F. Mertens, "Erroneously Low Results Due to High Nonspecific Binding Encountered with a Radioassay Kit that Measures 'True' Serum Vitamin B$_{12}$", Am. J. Clin. Pathol. 74:209:213 (1980).

D. F. M. Van De Wiel, W. Th. Goedemans and M. G. Woldring, "Production and Purification of Antibody Against Protein-Vitamin B$_{12}$ Conjugates for Radioimmunoassay Purposes", Clinica Chimica Acta, 56:143–149 (1974).

D. B. Endres, K. Painter and G. D. Niswender, "A Solid-Phase Radioimmunoassay for Vitamin B$_{12}$ in Serum, With Use of Radioiodinated Tyrosine Methyl Ester of Vitamin B$_{12}$", Clin. Chem. 24(3):460–465 (1978).

Kricka, L. Ligand Binder Assays, pp. 141-143 & 165, Marcel Dekkar, Inc. NY NY 1985.

Gottlieb, C. Blood, vol. 25, No. 6 (June):875-883 1965.

Kipps, T. Schemata for the production of monoclonal antibody producing hybridomas pp. 108.1–108.9; Blackwell Scientific Publications, Palo Alto, CA 1967.

Samloff, M., et al, J. Immunol., vol. 101, No. 3, pp. 578–586, 1968.

Monoclonal Antibody Technology, A. M. Campbell, Elsevier Science Publishers, Amsterdam, The Netherlands, pp. 1–5, 1984.

*Primary Examiner*—Toni R. Scheiner
*Attorney, Agent, or Firm*—Sprung Horn Kramer & Woods

[57] ABSTRACT

A competitive immunoassay for vitamin B$_{12}$ using labeled monoclonal antibodies to the vitamin B$_{12}$ binding site on intrinsic factor and labeled intrinsic factor.

9 Claims, 3 Drawing Sheets

VITAMIN B12 ASSAY

This is a continuation of application Ser. No. 07/371,234, filed Jun. 26, 1989 now abandoned.

BACKGROUND OF THE INVENTION

Vitamin $B_{12}$ (cyanocobalamin) has an empirical formula of $C_{63}H_{88}O_{14}N_{14}PCo$ (Mol. Wt. 1355.4 daltons) and is a complex molecule having three major components: a porphyrin-like ring structure consisting of four reduced and extensively substituted pyrrole rings (designated A to D) surrounding a single cobalt atom; an α-5,6-dimethylbenzimidazole ribonucleotide group which links to the corrin nucleus with bonds to the cobalt atom and to the propionate side chain of the D ring; and a variable R group which can be cyanide, hydroxyl, methyl or 5-deoxyadenosyl. The cyano-substitution is an artifact of isolation but is the form which is currently assayed. Hydroxycobalamin, methylcobalamin and 5-deoxyadenosylcobalamin are the physiologically active coenzyme forms of vitamin $B_{12}$. The two major active cobalamins, methylcobalamin and 5-deoxyadenosylcobalamin, are essential for DNA biosynthesis, replication and cell growth.

Dietary vitamin $B_{12}$, in the presence of gastric acids and pancreatic proteases, is released from intestinal R protein-like binding proteins and is immediately bound to intrinsic factor (IF), the gastrointestinal binding glycoprotein responsible for the specific binding and absorption of vitamin $B_{12}$. Intrinsic factor has a molecular weight of approximately 40,000 and differs markedly in structure from the R proteins. Its ability to bind vitamin $B_{12}$ at the exclusion of metabolically inactive cobinamide has led to the predominant use of this binding protein in the commercially available vitamin $B_{12}$ assays. The IF:vitamin $B_{12}$ complex interacts with the ileal mucosal cells and is then absorbed into the blood stream.

Following absorption, all three active cobalamins are present in plasma bound to plasma-binding proteins known as transcobalamin II and R proteins (also known as nonintrinsic factors). Transcobalamin II binds approximately 20% of the total plasma vitamin $B_{12}$ while the remainder is bound to the R proteins. Vitamin $B_{12}$ bound to transcobalamin II, is rapidly cleared from the plasma and delivered to a variety of cells, such as the hepatic parenchymal cells of the liver. The R proteins may also play a role in the delayed transport and cellular delivery of vitamin $B_{12}$ to the liver. Because of the high affinity with which the plasma-binding proteins bind vitamin $B_{12}$, the denaturation of these proteins is necessary in the performance of cyanocobalamin assays.

Vitamin $B_{12}$ deficiency is due primarily to a disruption of IF:vitamin $B_{12}$ binding resulting from a failure of parietal cell production of intrinsic factor or the production of anti-intrinsic factor antibodies. The failure of parietal cells is probably due to the presence of cytotoxic autoantibodies. Serum antibodies to intrinsic factor have been extensively studied. Two types of antibodies have been identified: the blocking antibody (Type I), which blocks the binding of vitamin $B_{12}$ to IF and a nonblocking antibody (Type II), which reacts with the IF:vitamin $B_{12}$ complex. Serum blocking antibodies are present in 50–76% of vitamin $B_{12}$ deficient patients and have a high degree of specificity for the diagnosis of pernicious anemia. Commercial assay kits which measure the levels of these anti-IF antibodies are available (Corning ImmoPhase IFAB) and studies on the utility of these assays in the differential diagnosis of vitamin $B_{12}$ deficiency have proceeded to the present.

Vitamin $B_{12}$ deficiency is more commonly caused by defective gastrointestinal absorption than from a deficient diet. Therefore, additional factors which can lead to vitamin $B_{12}$ malabsorption include the combination of gastric achlorhydria and decreased secretion of IF secondary to gastric atrophy or surgery, intestinal parasites, bacterial gastroenteritis and intestinal malignancies. Other disorders which may account for a vitamin $B_{12}$ deficiency include dietary deprivation (veganism), drugs, organ disease (liver), hyperthyroidism and transcobalamin II aberrations.

A deficiency in vitamin $B_{12}$ can lead to disease states marked by defective DNA synthesis culminating in delayed cellular mitosis. Since the cells having the most rapid metabolism will be the most dramatically affected, the hematopoietic system is particularly sensitive to vitamin $B_{12}$ deficiencies. The primary clinical manifestation of this vitamin deficiency is the development of a megaloblastic anemia which is also known as pernicious anemia. Vitamin $B_{12}$ is also implicated in the maintenance of the myelin of the nervous system. For these reasons, it is very important to be able to diagnose vitamin $B_{12}$ deficiencies.

The current state of the art regarding vitamin $B_{12}$ assays utilizes a wide variety of assay techniques. Microbial assays are based upon the principle that some microorganisms such as *Euglena gracilis* and *Lactobacillus leichmannii* require vitamin $B_{12}$ for normal growth and replication. Standard curves are produced using known amounts of vitamin $B_{12}$ and bacterial growth produced by a sample containing an unknown amount of vitamin $B_{12}$ is compared with the standard curve. Bacterial growth can be measured in numerous ways but the most common is turbidimetric measurement.

The deoxyuridine suppression test is performed on bone marrow cells which have been aspirated from the patient. A vitamin $B_{12}$ deficiency is noted if there is a reduction in the suppression of radioactive iododeoxyuridine incorporation into DNA by deoxyuridine.

High-performance liquid chromatography is based upon the variability in the rate of travel of different compounds through a medium under pressure within a column. The elutes are then detected at picogram/ml concentrations by ultra-violet or other detectors such as fluorescence and electrochemical detection.

Another method involves the use of antisera specific to vitamin $B_{12}$ which are employed in specific radioimmunoassays to directly measure the liberated vitamin.

Still another method involves competitive protein-binding radioimmunoassays (radioisotopic dilution assays). These assays have the prerequisite that the vitamin $B_{12}$ in the sample be freed from its binding proteins by physical, chemical or enzymatic denaturation or digestion. The most commonly used methods are the boil method which involves boiling the sample for 15–30 minutes and the non-boil method which involves the use of highly alkaline buffer solutions containing KCN which simultaneously denature the binding proteins and convert the cobalamins to the stable cyanocobalamin form. Both the boil and the non-boil methods use radioactive ($^{57}$Co-labelled) vitamin $B_{12}$ in a competitive system which employs purified hog intrinsic factor as the binding agent and a separation step to remove unbound sample vitamin $B_{12}$.

In spite of the fact that there are numerous vitamin $B_{12}$ assays currently available, there remains a continuing need for an improved assay that will overcome the shortcomings of the state of the art techniques. These shortcomings include a lack of sensitivity, difficulties encountered in standardization and the impracticality of use in high volume situations, i.e. in hospitals. Further, there are no commercial non-isotopic immunoassays for this analyte on the market. During the past decade, major attempts have been made by numerous groups to produce such a non-isotopic test for vitamin $B_{12}$. These attempts have been unsuccessful, due primarily to the small size and complexity of the vitamin $B_{12}$ molecule. Therefore, there is a current need for an accurate, precise and reliable reference method for assaying cyanocobalamin. This invention is intended to address that need.

SUMMARY OF THE INVENTION

This invention pertains to the development of a process and an immunoassay for the determination of the concentration of vitamin $B_{12}$ in a sample. The process can be performed manually such as by means of a diagnostic kit or automatically such as in an automatic analyzer.

In particular, this invention in one aspect pertains to the production and isolation of monoclonal antibodies specific to the intrinsic factor:vitamin $B_{12}$ complex and in another aspect to the production and isolation of monoclonal antibodies specific to the vitamin $B_{12}$ binding site on intrinsic factor. Further, this invention is directed at the production and isolation of monoclonal antibody lines capable of producing these antibodies.

DETAILED DESCRIPTION OF THE INVENTION

Figure 1:
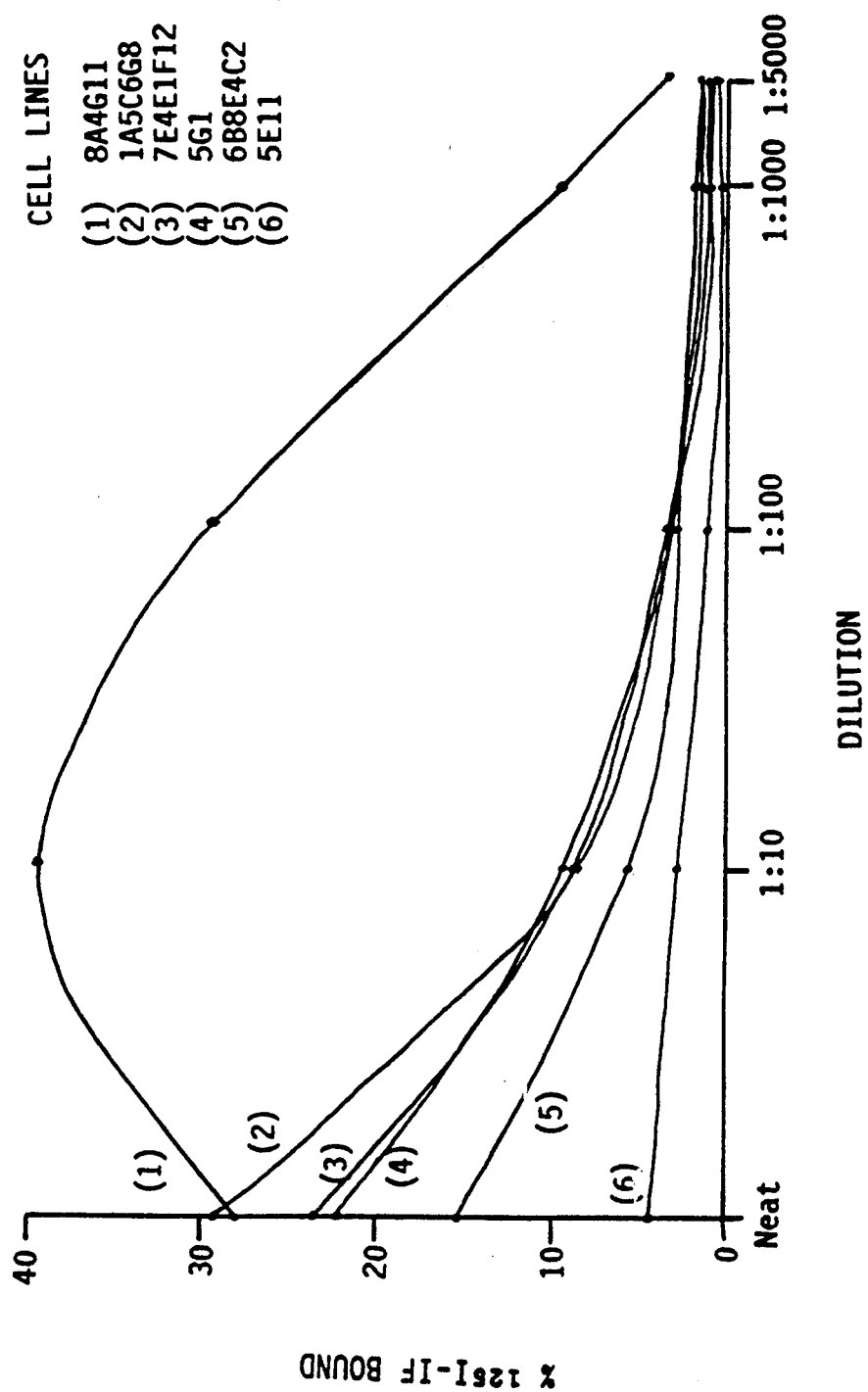
FIG. 1 is a titer curve for several monoclonal antibody cell lines, depicting the percentage of $^{125}I$-IF bound versus the amount of antibody dilution.

This invention provides for the development of a process and an immunoassay for determination of the concentration of vitamin $B_{12}$ in serum or other body fluids which involves the use of novel monoclonal antibodies. The preferred embodiment of this invention pertains to the production of monoclonal antibodies specific to the vitamin $B_{12}$ binding site on intrinsic factor. In a competitive assay, vitamin $B_{12}$ would compete with labelled monoclonal antibodies for binding to intrinsic factor. Use of these site-specific antibodies in such an assay, enables indirect measurement of vitamin $B_{12}$, as the vitamin $B_{12}$ levels are measured by monitoring antibody binding to IF. The amount of antibody bound is inversely proportional to the amount of vitamin $B_{12}$ present. The sample is first boiled or pretreated with a denaturing solution (non-boil method) to release vitamin $B_{12}$ from its binding proteins, to which it is strongly bound. Following denaturation, the "site specific" monoclonal antibody reagent and labelled intrinsic factor are added and incubated with the sample.

Another embodiment of the invention pertains to the production of monoclonal antibodies specific to the IF:vitamin $B_{12}$ complex and use of these antibodies to identify the IF:vitamin $B_{12}$ complex. Sample preparation is identical to that for the embodiment described above. Binding of the sample vitamin $B_{12}$ is accomplished by labelled IF. The antibodies to the IF:vitamin $B_{12}$ complex are labelled for use in identification of the IF:vitamin $B_{12}$ complex and separation is accomplished by standard methods. Monoclonal antibody binding is in direct proportion to the amount of sample vitamin $B_{12}$ present.

Labelling of intrinsic factor and the monoclonal antibodies can be done by incorporating labels commonly used in state of the art immunoassays, such as hapten molecules, radioactive atoms or groups, enzymes, vitamins (biotin), dyestuff or fluorescent groups. This labelling is usually performed before any immunological reaction is allowed to take place. However, it may be performed at a later stage by allowing the component which must be labelled to react with the corresponding binding partner, which has previously been labelled. The coupling of the enzyme/dyestuff/fluorogen/ can be brought about in a known way, for example by the formation of an amide linkage. Labelling with a radioisotope can also be performed by methods well established in the art. Useful isotopes include, without limitation, $^{125}I$, $^{131}I$, $^{14}C$ and $^{3}H$.

In the preferred embodiment, one of the labels used is a signal generating label for use in detection and the other label is capable of being captured by a capture ligand on a solid phase. For example, intrinsic factor can be labelled with an enzyme and the monoclonal antibodies labelled with a hapten, or vice versa. Preferably, the enzymes are those which can be colorimetrically, electrochemically, spectrophometrically or fluorometrically determined. These include, without limitation, alkaline phosphatase, acetylcholinesterase, malate dehydrogenase, egg white lysozyme, horseradish peroxidase and $\beta$-galactosidase. The preferred hapten molecule is a fluorogenic molecule, for example fluorescein isothiocyanate (FITC).

The preferred solid phase is magnetizable particles, but this invention also contemplates the use of filter paper, plastic beads, or test tubes made from polyethylene, polystyrene, polypropylene or other suitable materials. Also useful are particulate materials such as agarose, crosslinked dextran, and other polysaccharides. Techniques for binding to the solid phase are also well known in the art. Numerous solid support materials and binding methods can be used, examples of which are described in U.S. Pat. No. 4,659,678, incorporated herein by reference.

Separation of the complexes may be by any of a variety of physical, chemical or immunological techniques. Likewise, any of the common substrates known in the immunoassay art may be used. The preferred separation procedure uses antibodies linked to magnetizable particles. Examples include the fluorescein antibody magnetizable particle (FAMP) method as described in S. J. Rattle et al., Clin. Chem. 30(9): 1457-1461 (1984) or double antibody magnetic particle separation, using anti-mouse labelled magnetic particles as described in U.S. Pat. No. 4,659,678. Another suitable separation procedure is the covalently linked antibody magnetic particle separation method, which involves mixing the antigen-containing sample with two monoclonal antibodies raised against different epitopes of the antigen, where one monoclonal antibody is enzyme labelled and the other is covalently bound to a polyclonal antibody raised against FITC, which is subsequently covalently bound to magnetizable particles. Other separation procedures may also be suitable.

In both embodiments of the present invention, it may be necessary to utilize labelled antibodies specific for alternate determinant sites on IF in order to identify the (IF:vitamin $B_{12}$) (monoclonal antibody) complex.

It is possible to amplify the sensitivity of immunoassays using monoclonal antibodies of this invention in numerous fashions. Typical examples are enzyme amplification, Stanley et al., Am. Biotechnol. Lab. 3: 48–53 (1985), and the biotin-avidin method, L. A. Sternberger, Immunocytochemistry, 2nd ed., John Wiley & Sons (1979). These designs will theoretically yield the desired sensitivity because the primary reagents are combined in solution prior to separation.

The vitamin $B_{12}$ immunoassay utilizing monoclonal antibodies to the vitamin $B_{12}$ binding site on IF involves the following steps:

treating a sample of the fluid to free vitamin $B_{12}$ from the binding proteins;

contacting the sample with labelled monoclonal antibodies specific to the vitamin $B_{12}$ binding site on intrinsic factor and labelled intrinsic factor, to form intrinsic factor:antibody and intrinsic factor:vitamin $B_{12}$ complexes;

adding a solid phase to said complexes to form bound and unbound complexes;

separating the bound and unbound complexes and washing; and measuring either the amount of bound complex or unbound complex to quantify the amount of vitamin $B_{12}$ present in the sample. If the amount of intrinsic factor:antibody is measured, the value will be inversely proportional to the amount of vitamin $B_{12}$ present in the sample. If the intrinsic factor:vitamin $B_{12}$ is measured, the value is directly proportional.

Accordingly, an immunoassay of this embodiment of the invention would comprise (1) monoclonal antibodies that bind to the vitamin $B_{12}$ binding site on intrinsic factor and block the binding of vitamin $B_{12}$ to intrinsic factor said monoclonal antibodies being labelled with a first label, (2) intrinsic factor labelled with a second label and (3) a solid phase containing a capture ligand for one of said labels with the other label being a signal generating label for use in detection. The process itself is illustrated in Example 1. For purposes of illustration only, the monoclonal antibodies are labelled with FITC, intrinsic factor is enzyme labelled. Separation is done by the FAMP method, so magnetizable particles are used as the solid phase with antibodies specific to FITC being the capture ligand. These steps are not intended to limit the invention in any manner but are merely illustrative of an assay that can be developed using these novel monoclonal antibodies.

EXAMPLE 1

1. The sample containing the vitamin $B_{12}$ ($B_{12}$) analyte bound to the binding proteins, is chemically or physically (e.g. heat or change in pH) pretreated. This pretreatment frees the analyte, resulting in a sample containing free vitamin $B_{12}$ and the denatured binding proteins.

2. The sample is mixed with FITC conjugated monoclonal antibodies (FITC-MAb) which are specific to the IF binding site and subsequently incubated with enzyme labelled intrinsic factor (IF-EZ). This is a competitive step since the vitamin $B_{12}$ "competes" with the monoclonal antibodies for binding to IF.

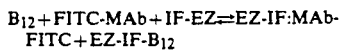

3. Antibodies specific to the label used on the monoclonal antibodies, in this instance FITC ($\alpha$-FITC), coupled to magnetizable particles (MP) are added in excess.

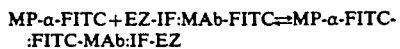

4. The captured complexes are then separated by magnetic particle separation and washed to remove the free IF-EZ.

5. The signal from the MP-bound complex is then measured spectrophometrically following the addition of a substrate reagent such as pNPP and/or an amplification reagent. The color intensity obtained is inversely proportional to the vitamin $B_{12}$ concentration.

The vitamin $B_{12}$ immunoassay utilizing monoclonal antibodies to the IF:vitamin $B_{12}$ complex involves the following steps:

treating a sample of the fluid to free vitamin $B_{12}$ from the binding proteins;

contacting the sample with labelled intrinsic factor, in excess, and labelled monoclonal antibodies specific to the intrinsic factor:vitamin $B_{12}$ complex, in excess, to form intrinsic factor:vitamin $B_{12}$:antibody complexes;

adding a solid phase to said complexes to form bound and unbound complexes;

separating the bound and unbound complexes and washing; and measuring either the amount of bound complex or unbound complex to quantify the amount of vitamin $B_{12}$ present in the sample. If the amount of intrinsic factor:vitamin $B_{12}$:monoclonal antibody is measured, the value will be directly proportional to the amount of vitamin $B_{12}$ in the sample. If the amount of excess monoclonal antibodies is measured, the value will be inversely proportional.

Accordingly, an immunoassay of this embodiment of the invention would comprise (1) monoclonal antibodies that bind to the intrinsic factor:vitamin $B_{12}$ complex said monoclonal antibodies being labelled with a first label, (2) intrinsic factor labelled with a second label and (3) a solid phase containing a capture ligand for one of said labels with the other label being a signal generating label for use in detection. The process itself is illustrated in Example 2. The intrinsic factor is labelled with FITC and the monoclonal antibodies are enzyme labelled. Separation is by the FAMP method. Once again, these parameters are merely illustrative and are not intended to limit the invention in any manner.

EXAMPLE 2

1. The sample, containing the vitamin $B_{12}$ ($B_{12}$) analyte bound to the binding proteins, is chemically or physically (e.g. heat or change in pH) pretreated. This pretreatment frees the analyte, resulting in a sample containing vitamin $B_{12}$ and free denatured binding proteins.

2. The sample is then mixed and subsequently incubated with an excess of FITC conjugated intrinsic factor (FITC-IF) together with an excess of enzyme labelled monoclonal antibodies (EZ-MAb) which recognize the IF:vitamin $B_{12}$ complex.

$B_{12}$ + FITC-IF +

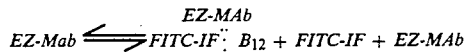

3. Antibodies specific to the label used on intrinsic factor, in this instance FITC (α-FITC), coupled to magnetizable particles (MP) are added to the sample in excess to separate the complexes.

4. The captured complexes are then separated by magnetic particle separation and washed to remove the free EZ-MAb.

5. The signal from the labelled monoclonal antibodies in the bound complex is then measured spectrophotometrically following the addition of a substrate reagent such as pNPP and/or an amplification reagent. The color intensity obtained is directly proportional to the vitamin $B_{12}$ concentration.

The method of obtaining the monoclonal antibodies of this invention is that discussed by Kohler and Milstein in Nature 256: 495–497 (1975). Summarized briefly, this process involves injecting an animal with an immunogen (Example 3 and 4). The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen (Example 5). In this manner, the individual antibody species obtained, are the product of a single B cell from the immune animal generated in response to a specific site recognized on the immunogenic substance. This method is best described with reference to the following examples, which are merely illustrative of the present invention and should not be considered as limiting the scope of the invention in any manner.

Preparation of the IF:vitamin $B_{12}$ complex is accomplished by mixing commercially available highly purified hog intrinsic factor with an excess of vitamin $B_{12}$, to insure maximum complex formation. The free vitamin $B_{12}$ is then separated by standard gel filtration techniques or dialysis and the IF:vitamin $B_{12}$ complex can then be used as the immunogen to produce monoclonal antibodies to the complex.

EXAMPLE 3

Preparation of Immunogen

The IF:vitamin $B_{12}$ complex immunogen was prepared using a calculated 1:1 molar ratio of IF to vitamin $B_{12}$ (1 mg IF binds 30 μg vitamin $B_{12}$). Eight hundred eighty micrograms of IF (16 nM) was combined with 26.4 μg of vitamin $B_{12}$ (19.48 nM) in 0.1M $NaH_2PO_4$ (pH 7.5). The calculated molar ratio of vitamin $B_{12}$ to IF was 1.22:1. This combination was brought to 2 ml with monobasic phosphate buffer, covered and refrigerated overnight. The immunogen was then purified by FPLC (Pharmacia). Subsequent UV spectrophotometry on the purified complex gave a calculated final molar ratio of 1.2:1 with a 96% recovery (850 μg). The purity of the immunogen was also determined using native PAGE electrophoresis and the molecular weight was determined by comparison with protein calibrators using high pressure liquid chromatography (Hewlett Packard 1090M).

Standard techniques can be employed to select clonal hybridoma cell lines producing monoclonal antibodies to the IF:vitamin $B_{12}$ complex and to the vitamin $B_{12}$ binding site on intrinsic factor.

EXAMPLE 4

Immunization Protocol

Eight mice to be immunized with the IF:vitamin $B_{12}$ complex were divided into two groups of four each. The first group received 100 μl of immunogen containing 50 μl of the purified IF:vitamin $B_{12}$ complex (27 μg) and 50 μl of Ribi adjuvant (Ribi ImmunoChem Research, Inc., Hamilton, Mont.). These injections were given by foot pad and by multiple subcutaneous injections in the inguinal and axillary regions. The second group of four mice received 100 μl of the same preparation via multiple intramuscular and intraperitoneal routes.

Six mice were selected and divided into two groups of three each for immunization with purified IF. The first group received 100 μl of immunogen containing 50 μl (25 μg) of IF and 50 μl of Ribi adjuvant/mouse/immunization. These injections were given in the foot pad and subcutaneously at multiple sites in the inguinal and axillary regions. The second group of three received injections of IF at multiple intramuscular and intraperitoneal sites (100 μl total volume).

A schedule of immunizations and bleeds was established to insure a minimum of 3 bouts of exposure. Prebleeds and test bleeds were evaluated for presence of polyclonal antibodies by screening on antigen coated plates (Costar vinyl).

Following the third immunization, the mouse having the highest serum binding to IF (mouse B2) and the mouse with the highest binding to solid phase IF from the group receiving the IF:vitamin $B_{12}$ complexes (mouse D4) were selected for IV boost and sacrifice. Fusions were carried out using the principles outlined in Kohler and Milstein, Nature 256: 495–497 (1975).

Screening techniques were devised to select specific hybridoma cell lines capable of producing monoclonal antibodies to the IF:vitamin $B_{12}$ complex and to the vitamin $B_{12}$ binding site on intrinsic factor.

EXAMPLE 5

Screening and Clone Selection

Sera and supernate screening was performed on duplicate microtiter plates which had been precoated with 100 ng/50 μl well of IF in carbonate-bicarbonate buffer (50 mM, pH 9.6) and 100 ng/50 μl well of IF:vitamin $B_{12}$ complex. The plates were incubated at room temperature for 24–48 hours and were then washed three times and blocked with 52 μl of 2% powdered milk in water. The plates were then incubated for 1 hour at room temperature and were rewashed. Fifty microliters of cell culture supernate from each cell line was added to all the wells and was incubated for 1 hour. The plates were washed and 50 μl of a 1:10,000 dilution of goat anti-mouse-horseradish peroxidase (HRP) conjugate was added and incubated for 1 hour. A substrate for HRP (3,3',5,5'-tetramethylbenzidine) was then added and the colored reaction product was allowed to form for 30 minutes. The enzyme-substrate reaction was then stopped by the addition of 50 μl of 2M $H_2SO_4$ and the plates were read at 450 nm. This screening procedure permitted selection of several lines which had some degree of specificity for either IF or the IF:vitamin $B_{12}$ complex. This procedure, taken with example 8 permitted selection of lines having some degree of specificity for the vitamin $B_{12}$ binding site on IF. These cell lines were: 8A4; 6B8; 5G1; 7E4; 2G7; 5E1; 5E11; 1A5; 7H8 and 1G5.

EXAMPLE 6

Iodination of Intrinsic Factor

Intrinsic factor was labelled with $^{125}$I-Na using the well established chloramine-T method, as set forth in Hunter and Greenwood, Nature (London) 194: 495–496 (1962). Intrinsic factor (50 μg in 100 μl distilled water) was mixed with 1 mCi of $^{125}$I-Na (10 μl, Amersham). Chloramine-T (25 μg/25 μl of 0.1M $NaH_2PO_4$ buffer, pH 7.5) was then added and this mixture was incubated for 45 seconds. The reaction was then terminated by the addition of 60 μg (per 50 μl of the phosphate buffer) of sodium metabisulfite. One hundred microliters of the phosphate buffer was then added and the mixture was applied on a PD-10 column (Pharmacia) which had been previously equilibrated with phosphate buffer. The mixture was eluted with the buffer and 0.5 ml fractions were collected in 25×75 mm borosilicate tubes. Determination of $^{125}$I activity peaks indicated that fractions 2 and 3 contained 76% of the activity (38 μg/ml).

EXAMPLE 7

Characterization of Cell Culture Supernate for Monoclonal Antibody Titers

One hundred microliters of cell culture supernate diluted neat, 1:10, 1:100, 1:1000 and 1:5000 were added to duplicate tubes. This was followed immediately by the addition of 100 μl of $^{125}$I-IF tracer (543 pg/tube) which gave the total tube counts of approximately 10,000 cpm. Following a one hour incubation at room temperature, the bound fraction was separated using sheep anti-mouse magnetic particle (2 mg/100 μl) separation. The bound fractions were then counted on a multichannel radioisotope counter (IsoData 20/20). FIG. 1 illustrates the titer curves which were obtained employing the supernates from the cell lines selected (1A5, 6B8, 5E11, 8A4, 7E4 and 5G1).

EXAMPLE 8

Selection of IF Site Specific Antibodies

Figure 2:
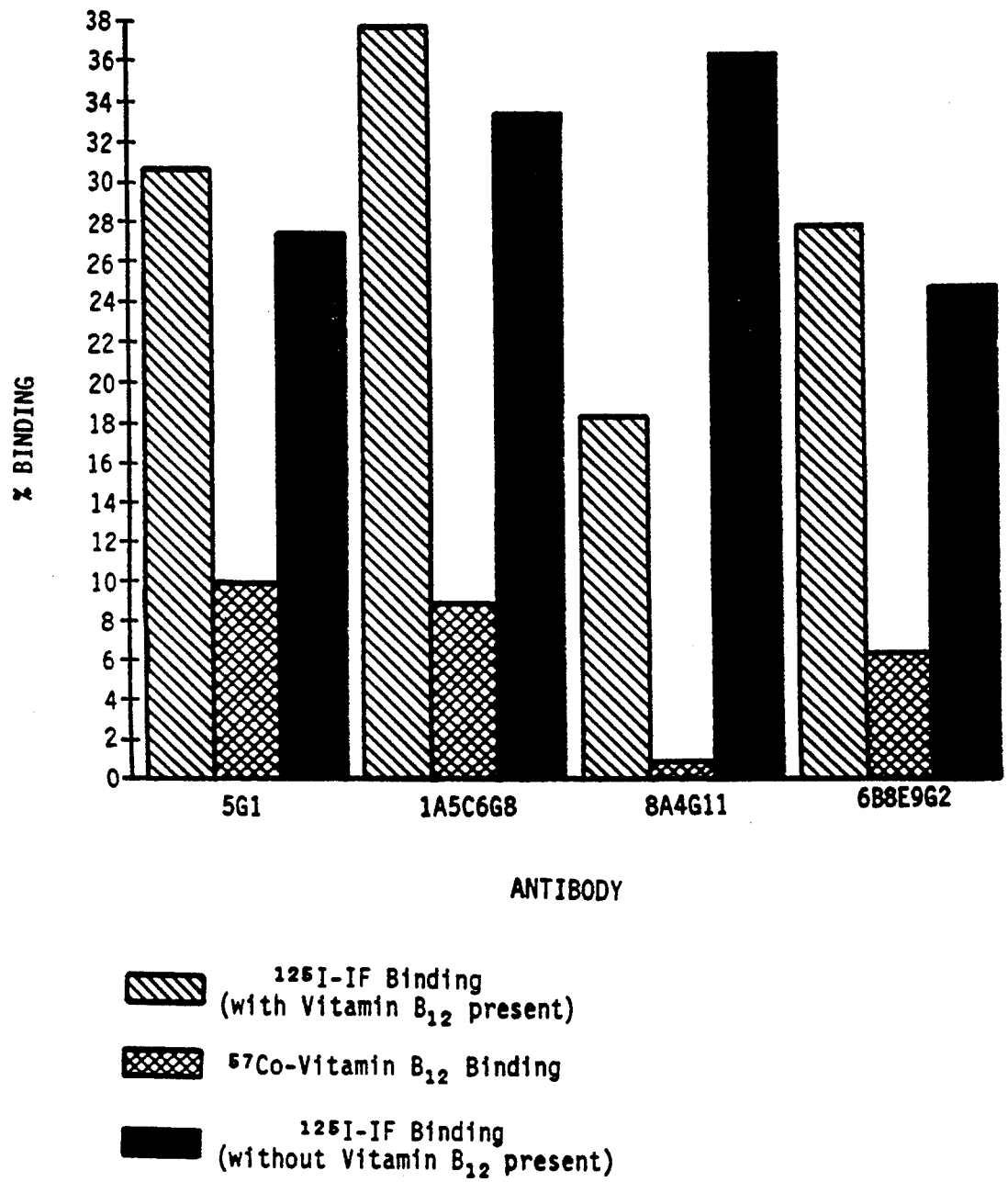
FIG. 2 is a bar graph illustrating the effect of different monoclonal antibodies on vitamin $B_{12}$ binding to intrinsic factor.
Figure 3:
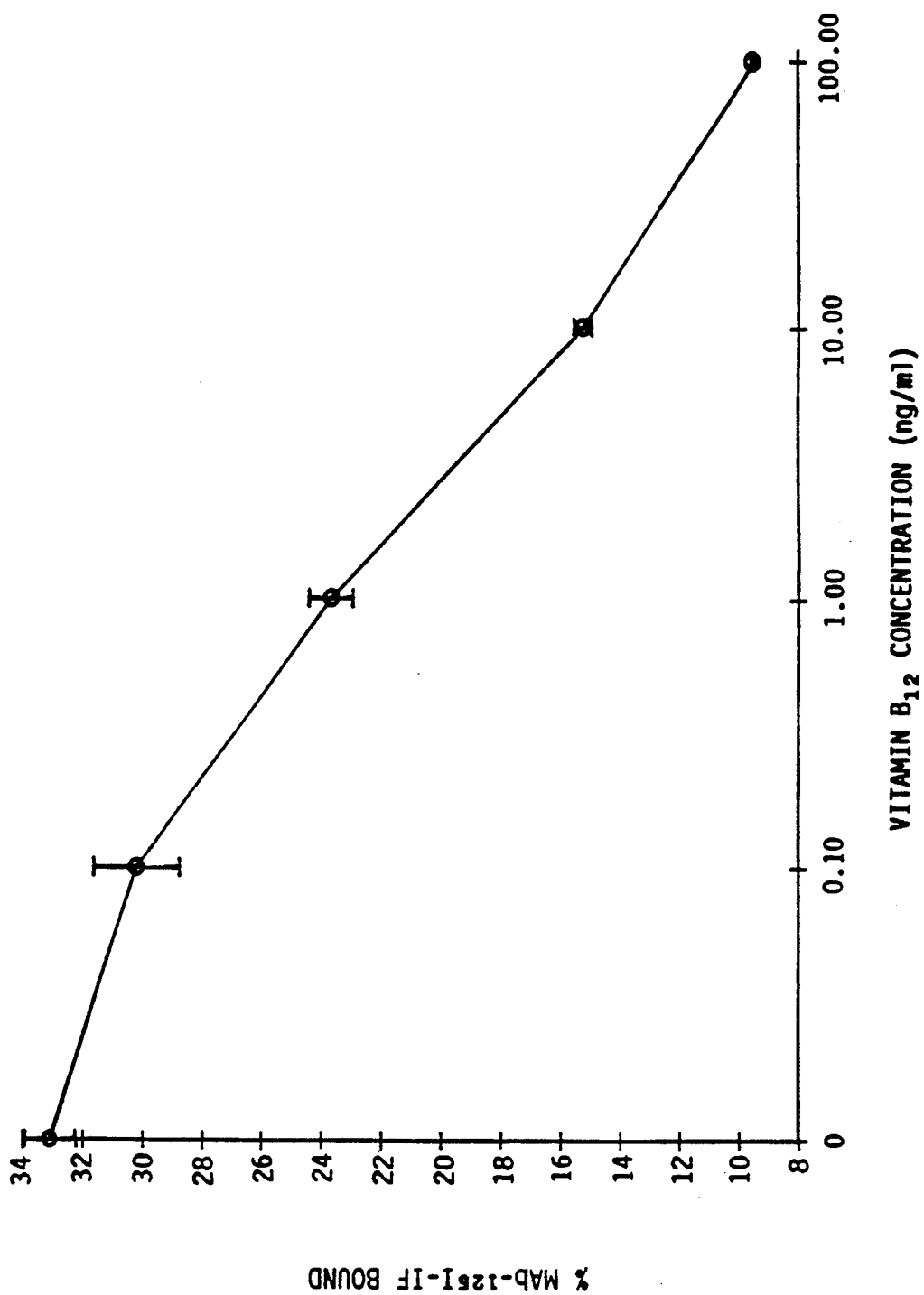
FIG. 3 is a calibration curve illustrating the specificity of the monoclonal antibodies of this invention for the vitamin $B_{12}$ binding site on IF.

In order to select antibodies specific for the IF:vitamin $B_{12}$ binding site and/or the IF:vitamin $B_{12}$ complex, selected supernates were utilized in differential binding studies. Inhibition of $^{57}$Co-labelled vitamin $B_{12}$ to intrinsic factor was demonstrated when monoclonal antibody 8A4G11 (expanded clone of the 8A4 cell line) was added in solution with $^{125}$I-IF. This is shown in FIG. 2, which also shows how this monoclonal antibody inhibited binding to a significantly greater degree than other monoclonal antibodies. Another study involved the addition of 100 μl of 0.1, 1, 10 and 100 ng/ml concentrations of vitamin $B_{12}$ (in distilled water); 100 μl of the appropriate dilution of monoclonal antibody supernate and 100 μl of $^{125}$I-IF (543 pg/tube) to duplicate tubes, followed by incubation for one hour. The bound complex was separated by addition of anti-mouse magnetic particles (2 mg/100 μl) after a 15 minute incubation. The calibration curves obtained showed the degree of specificity of monoclonal antibodies for the IF:vitamin $B_{12}$ binding sites and/or the IF:vitamin $B_{12}$ complex. FIG. 3 shows the calibration curve for monoclonal antibody 8A4G11 further demonstrating the specificity of this monoclonal antibody for the vitamin $B_{12}$ binding site on IF. The cell line 7H8 also provided monoclonal antibodies specific to the binding site. One other cell line (6B8) also showed displacement of vitamin $B_{12}$ which was not as pronounced as that shown by 8A4 and 7H8. The remaining antibodies were either specific for IF alone (5G1) or were preferentially specific for the IF:vitamin $B_{12}$ complex (7E4). The plate and tube screening results led to the initial selection of the following lines for ascites production in pristane primed mice: 8A4, 7H8, 1A5, 6B8, 7E4 and 5G1.

We claim:

1. An immunoassay kit for determining the concentration of vitamin $B_{12}$ in a sample comprising,
   a. monoclonal antibodies that are specific for the vitamin $B_{12}$ binding site on intrinsic factor and block the binding of vitamin $B_{12}$ to intrinsic factor said monoclonal antibodies being labelled with a first label;
   b. intrinsic factor labelled with a second different label; and
   c. a solid phase containing a capture ligand for one of said labels with the other label being a signal generating label for use in detection.

2. A complex wherein intrinsic factor having a first label is bound to a monoclonal antibody specific for the vitamin $B_{12}$ binding site on intrinsic factor thereby blocking the binding of vitamin $B_{12}$ to intrinsic factor, said monoclonal antibody having a second different label, where one of said labels is capable of being captured by a capture ligand on a solid phase and the other label is a signal generating label for use in detection.

3. A process for the determination of the concentration of vitamin $B_{12}$ in a fluid containing vitamin $B_{12}$ bound to binding proteins comprising the steps of:
   (a) treating a sample of the fluid to free vitamin $B_{12}$ from the binding proteins;
   (b) contacting the sample with labelled monoclonal antibodies specific to the vitamin $B_{12}$ binding site on intrinsic factor thereby blocking the binding of vitamin $B_{12}$ to intrinsic factor and labelled intrinsic factor which is labelled with a different label from that used with the monoclonal antibodies, one of the labels being capable of being bound by a capture ligand of a solid phase and the other label being a signal generating label to form intrinsic factor:antibody and intrinsic factor:vitamin $B_{12}$ complexes;
   (c) adding the solid phase containing the capture ligand for one of said labels to said complexes to form bound and unbound complexes;
   (d) separating the bound and unbound complexes and washing; and
   (e) measuring either the amount of bound complex or unbound complex to quantify the amount of vitamin $B_{12}$ present in the sample.

4. The process of claim 3 wherein the monoclonal antibodies are labelled with a hapten molecule.

5. The process of claim 4 wherein said hapten molecule is fluorescein isothiocyanate.

6. The process of claim 3 wherein said intrinsic factor is labelled with an enzyme.

7. The process of claim 3 wherein in step (e) the amount of intrinsic factor:antibody complex is measured, said value being inversely proportional to the amount of vitamin $B_{12}$ present in the sample.

8. The process of claim 3 wherein in step (e) the amount of intrinsic factor:vitamin $B_{12}$ complex is measured, said value being directly proportional to the amount of vitamin $B_{12}$ present in the sample.

9. The process of claim 3 wherein step (c) involves contacting the sample with antibodies specific to the label used for the monoclonal antibodies of step (b), coupled with magnetizable particles, to form a complex with the intrinsic factor:antibody complex, and the separation step (d) is by magnetic particle separation.

* * * * *